United States Patent [19]
Wilson et al.

[11] Patent Number: 5,593,899
[45] Date of Patent: Jan. 14, 1997

[54] DEVICE AND METHOD FOR MEASURING TISSUE OXYGENATION THROUGH THE SKIN USING OXYGEN DEPENDENT QUENCHING OF PHOSPHORESCENCE

[75] Inventors: David F. Wilson, Philadelphia, Pa.; Marek Pawlowski, Roslyn Heights, N.Y.

[73] Assignee: Trustees of the University of Pennsylvania, Philadelphia, Pa.

[21] Appl. No.: 278,880

[22] Filed: Jul. 22, 1994

Related U.S. Application Data

[63] Continuation-in-part of Ser. No. 22,190, Feb. 25, 1993, Pat. No. 5,501,225.

[51] Int. Cl.$^6$ ................................................ G01N 33/49
[52] U.S. Cl. ............... 436/127; 436/172; 422/82.08; 422/79; 422/80; 128/633; 128/664

[58] Field of Search ........................... 128/633, 664; 422/82.05, 82.08, 79–80; 436/127, 169, 172

[56] References Cited

U.S. PATENT DOCUMENTS

| | | | |
|---|---|---|---|
| 2,358,992 | 9/1944 | Millikan | 128/633 |
| 4,041,932 | 8/1977 | Fostick | 128/2 G |

*Primary Examiner*—Lyle A. Alexander
*Attorney, Agent, or Firm*—Duane, Morris & Heckscher

[57] ABSTRACT

Apparatus and method for measuring tissue oxygenation using oxygen dependent quenching phosphorescence. The apparatus comprises a phosphorescent probe applied to the surface of the skin; an oxygen impermeable film placed over the probe and the apparatus; a light excitation means for exciting the probe; a heating element for heating the probe; and an analyzer circuit for analyzing the output.

12 Claims, 6 Drawing Sheets

DEVICE AND METHOD FOR MEASURING TISSUE OXYGENATION THROUGH THE SKIN USING OXYGEN DEPENDENT QUENCHING OF PHOSPHORESCENCE

RELATED CASES AND CLAIM OF PRIORITY

This application is a continuation-in-part of U.S. Ser. No. 08/022,190, filed Feb. 25, 1993, now U.S. Pat. No. 5,501,225 entitled Imaging of Tissue Oxygen Using Needle Phosphorimeter.

FIELD OF THE INVENTION

The present invention generally relates to the imaging of the body portions of animals, and specifically to the field of phosphorimetry in biological applications.

BACKGROUND OF THE INVENTIONS

The present invention is based upon the phenomenon that oxygen has a quenching effect on the molecular luminescence of various chemical compounds and that this effect can be employed for imaging oxygen concentrations of the body portions of animals and humans. Animals, especially mammals, are dependent upon having adequate oxygen supplies in their body tissues. In mammals, the circulatory system employs specialized oxygen-carrying molecules in the blood to deliver oxygen from the lungs to other tissues throughout the body. Thus, every organ in the body contains oxygen in varying amounts and concentrations in every tissue. The distribution of oxygen in tissue can be indicative of structure, anomalies, defects or disease. U.S. Pat. No. 4,947,850 provides a detailed discussion of such technologies.

Co-pending U.S. Ser. No. 08/022,190 entitled Method and Apparatus for Oxygen Mapping discloses improved methods and apparatus for imaging internal body structures of animals. The apparatus and methods disclosed in this application are directed to measuring tissue oxygenation through the skin using oxygen dependent quenching of phosphorescence. In addition, there have been additional patents directed to this technology.

U.K. patent application No. GB 2,132,348A, published Jul. 4, 1984, disclose the use of fluorescent materials to measure levels of oxygen in blood both in vitro and in vivo using a fiber optic probe or catheter.

The prior art has disclosed indwelling devices for use during measurement of various blood parameters. For example, U.S. Pat. No. 3,787,119 discloses a catheter having a microlamp and a photosensitive element and other elements including a cup-like element for use in receiving blood and providing electrical output signals by means of wires extending through the catheter.

U.S. Pat. No. 3,814,081 discloses an optical measuring catheter employing fiber optic means for use in measuring oxygen saturation in blood, as well as blood pressure.

U.S. Pat. No. 4,200,110 discloses a fiber optic pH probe which includes an ion permeable membrane which encloses a guide containing solid material comprised of a hydrophilic copolymer having a pH sensitive dye attached thereto. The probe functions by optically detecting a change in color of the pH sensitive dye when excited by light. A phenol red dye is employed so that it absorbs light at a particular wavelength, with the amount of light being absorbed varying in dependence upon the pH level.

U.S. Pat. No. 4,476,870 discloses a fiberoptic oxygen partial pressure probe. This probe includes a hydrophobic gas permeable envelope which contains an adsorptive support which contains a fluorescent dye. Use of the probe for measuring partial pressure of gaseous oxygen in the bloodstream is based on the principle of dye fluorescent oxygen quenching. With the probe in place within a bloodstream, fluorescent dye is excited by light having blue wavelength, thus causing the dye to fluoresce at a green wavelength with the intensity of emitted light decreasing (quenching) with increasing levels of the partial pressure of gaseous oxygen in the bloodstream.

U.S. Pat. No. 5,127,405 discloses a fiber optic probe incorporating a luminescent composition which is used to monitor conditions of a subject. A response light from the fiber optic probe is detected and a frequency domain presentation of the response light is derived. Characteristics of the frequency domain representation are used to derive values for luminescent lifetimes or similar decay parameters and these values in turn are translated into the values of the conditions to be sensed.

Finally, U.S. Pat. No. 4,898,175 discloses an apparatus in which an illuminating light is fed by a device emitted from the tip part of an insertable endoscope. The endoscope is inserted into a body cavity and is radiated on to a part of the body to be observed. This illuminating light, having passed through a living body tissue, is imaged by an imaging device provided outside the body. The imaging device delivers a picture image signal to a signal processing device. The signal processing device processes the signal and outputs a video signal to a display device. This device displays the image observed within the living body. See also U.S. Pat. No. 4,947,850.

In addition to the above technologies, oxygen electrodes have also been designed for transcutaneous oxygen measurements. Oxygen electrodes, in contrast to systems which are based on the oxygen dependent quenching of phosphorescence, utilize substantial amounts of oxygen. The oxygen permeability of the skin is low and oxygen consumption by the electrodes can seriously deplete the oxygen pressure at the surface of the skin, resulting in measured oxygen values which are artificially low and which are strongly dependent upon blood flow in the immediate vicinity of the electrodes. In general, an oxygen electrode system must compensate by heating the skin to well above normal values in order to maximally dilate the vessels. In the phosphorescence method, the negligible oxygen consumption by the measuring system will permit the use of only one modest heating, primarily to overcome possible vasoconstriction due to depressed body temperature to assure uniform conditions among subjects. Oxygen electrodes further require calibration before each use. The calibration cannot alter with the time of measurement.

It would be desirable to provide an improved device and method for measuring oxygen pressure which could be applied to the outside of the skin and which could be used to obtain rapid and accurate oxygen pressure measurements. These and other objects of the present invention will become clear from the summary and detailed description which follow.

SUMMARY OF THE INVENTION

In accordance with the present invention, a system is provided for measuring tissue oxygenation using oxygen dependent quenching phosphorescence comprising: a phosphorescent probe applied to the surface of the skin of a patient; an oxygen impermeable film placed over said probe and skin; an optical head overlaying said oxygen impermeable film, said optical head comprising means for heating said impermeable film and said probe, means for providing an excitation light signal for exciting the probe such that said probe emits phosphorescent light, and a photodiode circuit which detects the phosphorescent light emitted by the probe and which outputs a signal characteristic of the oxygen decay of said skin proximate to said reflected phosphorescent signal.

In a further embodiment, the present invention is directed to apparatus for measuring tissue oxygenation through the skin using oxygen dependent quenching of phosphorescence comprising: a phosphorescent probe applied to the skin surface of a patient; an oxygen impermeable film overlaying said probe and for isolating the area of skin with the phosphorescent probe from ambient oxygen; an optical head overlaying said film, said optical head comprising a housing for covering said oxygen impermeable film and enclosing a light source for applying a single modulated excitation light for exciting said phosphorescent probe such that said probe emits an excitation light on the skin surface of said patient; a filter for filtering phosphorescent light from said skin; and a photodiode for receiving reflected filtered phosphorescent light and for outputting an electrical signal characteristic of phosphorescent decay for the patient such that said decay is characteristic of the oxygen pressure of said patient.

In yet a further embodiment, the present invention is directed to apparatus for measuring tissue oxygenation through the skin using oxygen dependent quenching of phosphorescence comprising: a phosphorescent probe applied to the skin surface of a patient; an oxygen impermeable polymeric film overlaying said probe for isolating the area of skin with the phosphorescent probe from ambient oxygen; a housing enclosing an optical head, said housing comprising a plastic cover covering said oxygen impermeable film, a light source for applying a single modulated excitation light for exciting said phosphorescent probe such that said probe emits a light on the skin surface of said patient, a filter for filtering said emitted phosphorescent light, a photodiode for receiving filtered phosphorescent light and for outputting an electrical signal characteristic of phosphorescent light time and oxygen pressure for the patient and a heater for heating the probe and skin of the patient.

The present invention is also directed to a method for measuring tissue oxygenation through the skin using oxygen dependent quenching of phosphorescence comprising the following steps: applying a phosphorescent probe applied to the skin surface of a patient; covering said probe with an oxygen impermeable film so as to isolate the area of skin with the phosphorescent probe from ambient oxygen; applying a single modulated excitation light for exciting said phosphorescent probe such that said probe emits an excitation light on the skin surface of said patient; filtering said emitted phosphorescent light; outputting an electrical signal characteristic of phosphorescent decay time and the oxygen pressure for the patient.

DETAILED DESCRIPTION OF THE PREFERRED EMBODIMENT

Figure 1:
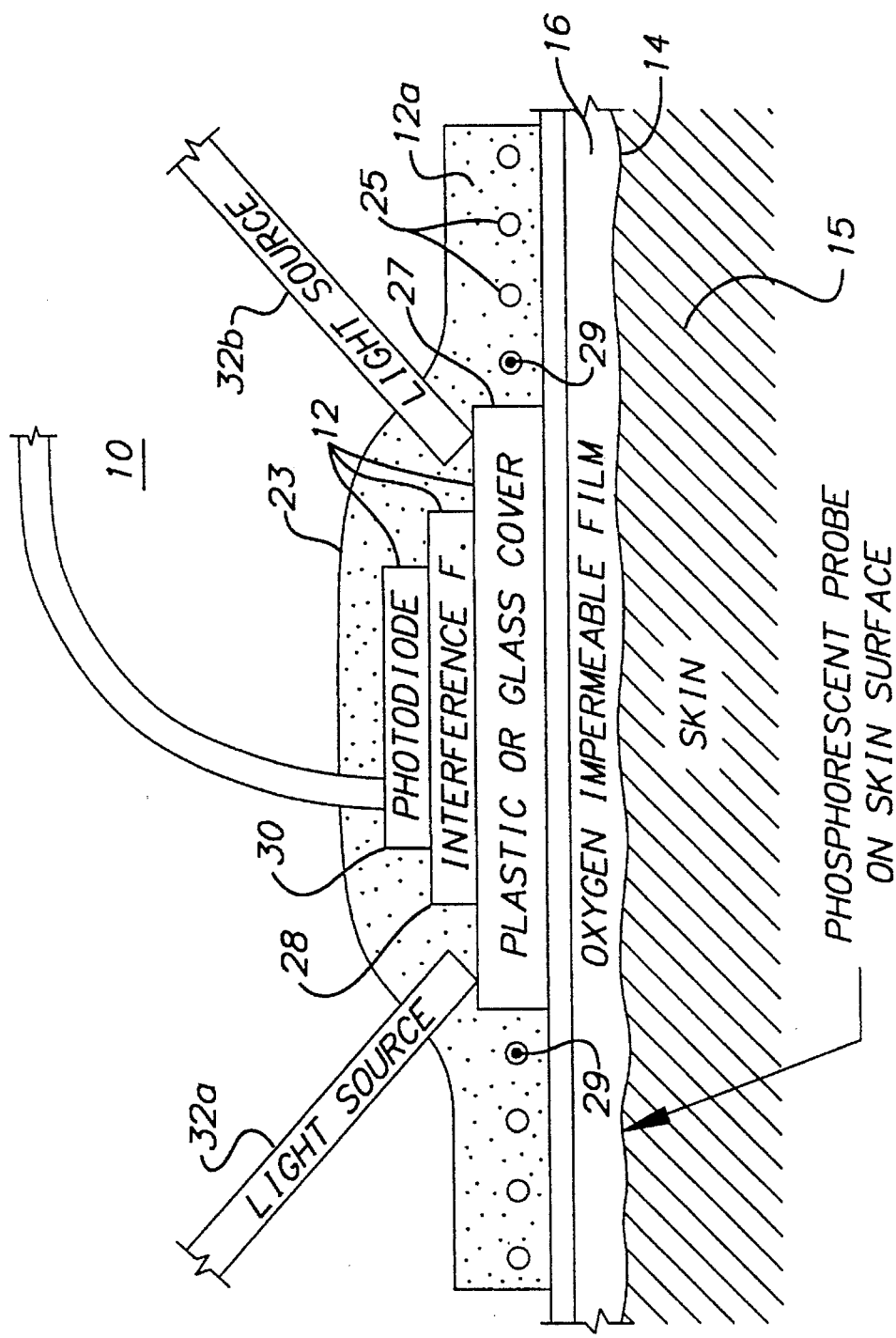
FIG. 1 is a phosphorescent probe in accordance with the present invention.
Figure 2:
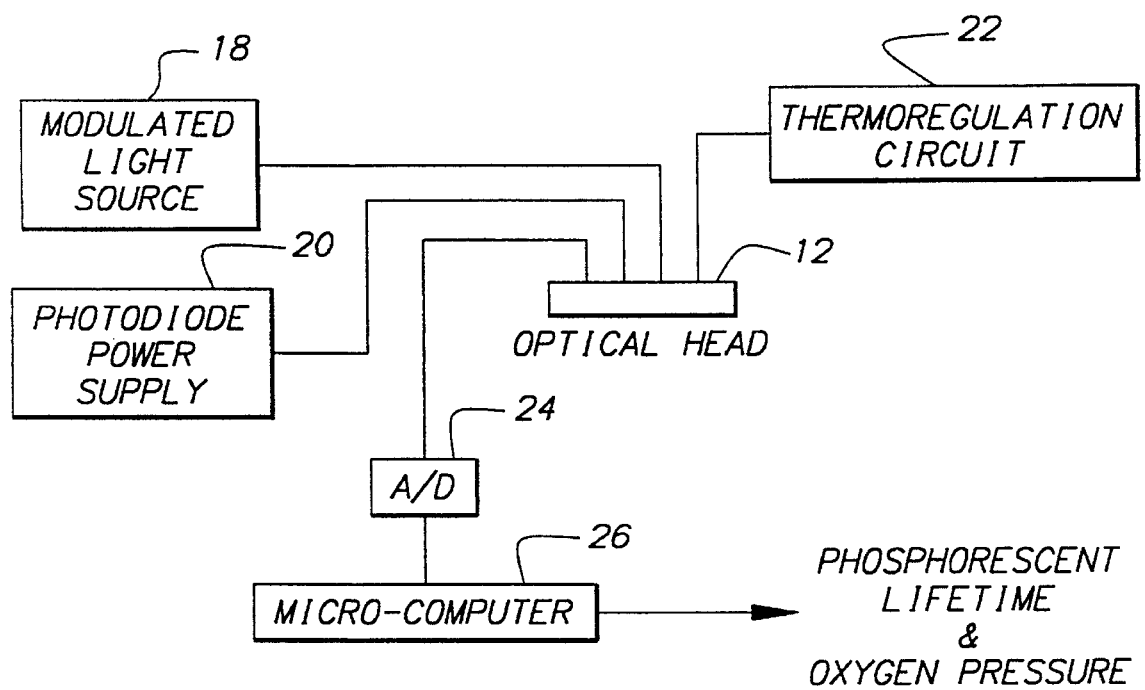
FIG. 2 is a block diagram of a system incorporating the device of the present invention.

The present invention is described with reference to the enclosed Figures wherein the same numerals are used where applicable. Referring to FIGS. 1 and 2, in a preferred embodiment, the present invention is directed to novel apparatus and system for determining oxygen concentration from a location external to the patient. The device 10 comprises a housing 23 including optical head 12 which is designed to be placed next to the skin of a patient, and which is coupled to analysis circuitry. A phosphorescent probe 14 is applied to the skin 15 of the patient and covered with an oxygen impermeable film 16. As will be discussed below, this phosphorescent probe can be applied within a skin cream. In a preferred embodiment, the device will be placed on the skin of a patient next to the arm or abdomen so as to cover the probe 14 and film 16.

The optical head 12 is coupled to a modulated light source 18, a photodiode power supply 20, a thermoregulation circuit 22, an analog to digital converter 24 and a microcomputer 26. These elements control the operation of the device. The microcomputer 26 stores software for analyzing data generated by the device.

Referring to FIG. 1, the optical head 12 of the present invention is described in detail. In a preferred embodiment, the optical head 12 overlays the oxygen impermeable film 16 and phosphorescent probe 14. The optical head 12 is encased within housing 23 which may be constructed from a polymer or plastic. The housing 23 also encloses a heat source 25 which heats the skin of the patient. The heat source, in a preferred embodiment, may comprise heating coils. The heat source 25 is connected to thermoregulation circuit 22. The thermoregulation circuit 22 preferably maintains the temperature of the system at between 39° and 42° C. within a variance of +0.1° C. This is slightly above normal body temperatures and keeps the blood vessels of the skin dilated. The housing 23 further encloses a light permeable glass or plastic cover 27 which in operation directly overlays the film 16, an interference filter 28 and a photodiode 30 to be described in detail below.

The phosphorescent probe 14 is now described in detail. The probe 14 preferably comprise one of a number of phosphorescent molecules having the required sensitivity to oxygen. The phosphorescent probe 14 will preferably comprise any composition from the family of chemicals known as porphyrins, chlorins, bacteriochlorin, porphyrinogen, and their derivatives. A particularly desirable probe is Pd-porphyrin.

Preferably, the probe 14 should be admixed with proteinaceous or albuminous compositions to improve the measurement of decay. The probe is preferably modified such that it can be included in any cream or oil base which is applied to the skin of the patient and yet be impermeable to the skin and remain on the surface. This leaves the phosphorescent probes in contact with the skin and within an appropriate oxygen sensitivity $T^o$ and Kq. The phosphorescent probe is preferably applied to a small area of the skin (about one centimeter in diameter), and the area covered with a film having a low oxygen permeability.

Oxygen impermeable film 16 comprises a plastic film which neither absorbs the excitation light nor the phosphorescent material in the probe 16. The plastic selected should have a low solubility for oxygen and a low diffusibility of oxygen. The film 16 preferably should be approximately three centimeters in diameter. The film 16 should have an adhesive surface when applied with the skin such that the film adheres tightly. Alternatively, the film could be taped into place on the skin. The function and purpose of the film 16 is to isolate the area of skin with the phosphorescent probe from oxygen in the air.

In a preferred embodiment the excitation light 18 originates from a single modulated source (flashlamp, light emitting diode or laser diode) filtered to give the desired wavelength of excitation light, i.e., between 400 and 700 nanometers. The excitation light 18 is applied as a flash of monochromatic light (a width at half-maximal intensity of less than five microseconds for flashlamps) which is directed onto the skin area with applied phosphor. The excitation light 18 is provided either by a light emitting diodes which are built into the optical head 12 or which are conducted to the optical head by a multifiber light guide 32a, 32b.

The emitted phosphorescence passes through filter 28 so as to fall on a photodiode. The photodiode current is analyzed to obtain the phosphorescent lifetime and the oxygen pressure calculated using the relationship $$T^o/T = 1 + Kq \times T^o \times PQ_2$$

where $T^o$ and $T$ are the phosphorescence lifetimes in the absence of oxygen and at an oxygen pressure $PQ_2$, respectively. $Kq$ is the quenching constant which relates to the frequency which the excited triplet state molecules collide with oxygen molecules and the probability that energy transfer will occur in any given collision.

The light guide should, in a preferred embodiment, be divided 32a, 32b to allow reflected light to be introduced from different sides of the photodiode so as to illuminate the sampled area as uniformly as possible. The present invention contemplates the use of more than one light emitting diode or laser diode if the excitation light intensity needs to be increased by the use of a ring of light.

As noted above, the present invention further includes a phosphorescent light filter 28 which is situated between the photodiode and plastic or glass cover. This element is preferably an interference filter or multi-layer dichroic filter 28 which filters the light which includes the excitation light scattered by the skin and some of the reflected light reaches the probe at the surface of the skin increasing the efficiency of the excitation process.

The photodiode 30 or detector of the present invention is now described. The photodiode 30 produces an electrical signal corresponding to the phosphorescent emission. The current from the photodiode or photo multiplier is used to determine the phosphorescence lifetime by one of several methods. The photodiode preferably should be 5 millimeters in diameter. Suitable detectors include avalanche photodiodes, a photomultiplier tube such as the R928, and microchannel plates such as manufactured by Hamamatsu Photonics, KK of Hamamatsu, Japan.

The outer core 12a of the optical head 12 is constructed of heat conductive material such as heat conductive plastic or aluminum with at least that part within heating source 25 and thermosensor 29 being 1–1.5 centimeters from the cover. A non-conductive material is used to cover the heat conductive core in order the minimize the energy required to maintain the temperature and minimize the sensing heat when the optical head is touched while it is in place and heated by heating source 25.

The resulting signal from the photodiode 30 is digitized by an analog to digital converter 24 such that the K of the signal may be determined by conventional analytic methods using the relationship $$T^o/T = 1 + Kq + T^o \times PQ_2$$

Figure 3:
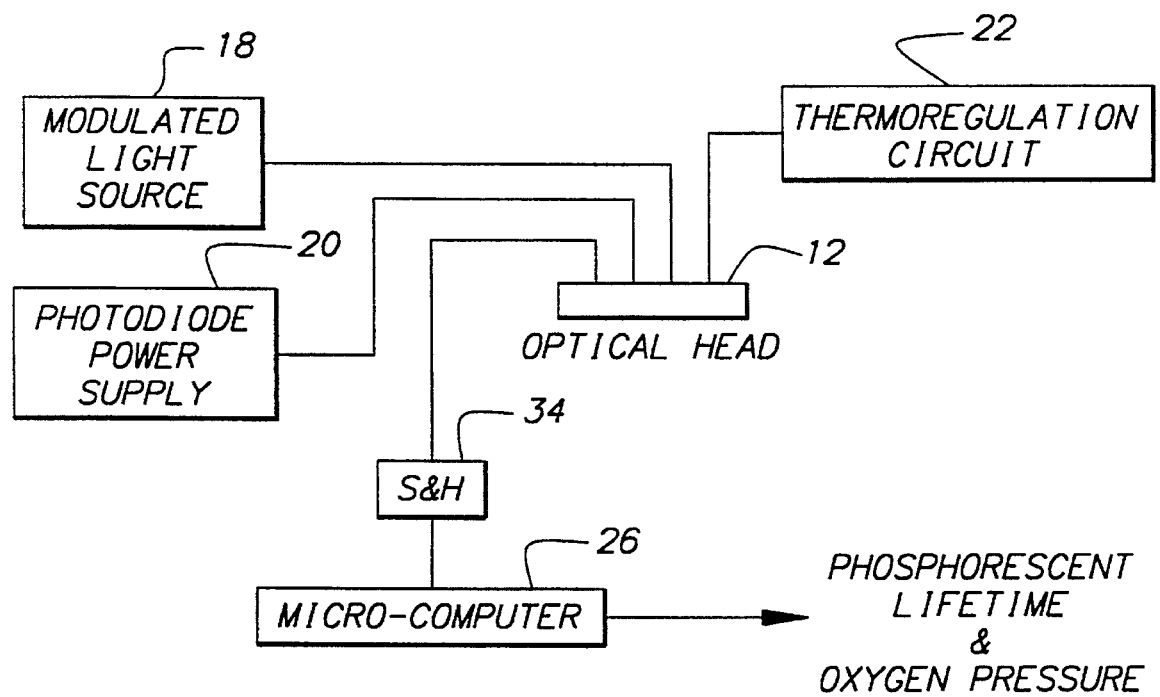
FIG. 3 is a block diagram of an alternative system of the present invention.

Alternatively, as shown in FIG. 3, sample and hold circuits 34 may be used to determine the phosphorescence intensities varying between different time intervals and the phosphorescent decays calculated.

Figure 3A:
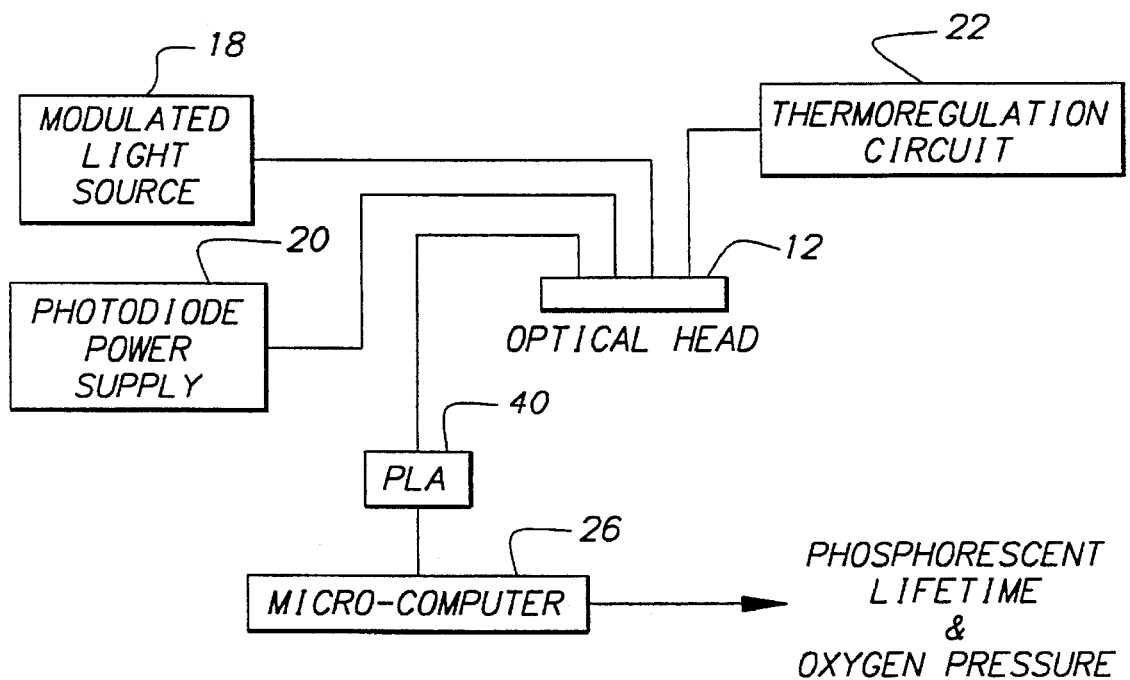
FIG. 3A is a block diagram of a second alternative system in accordance with the present invention.
Figure 4A:
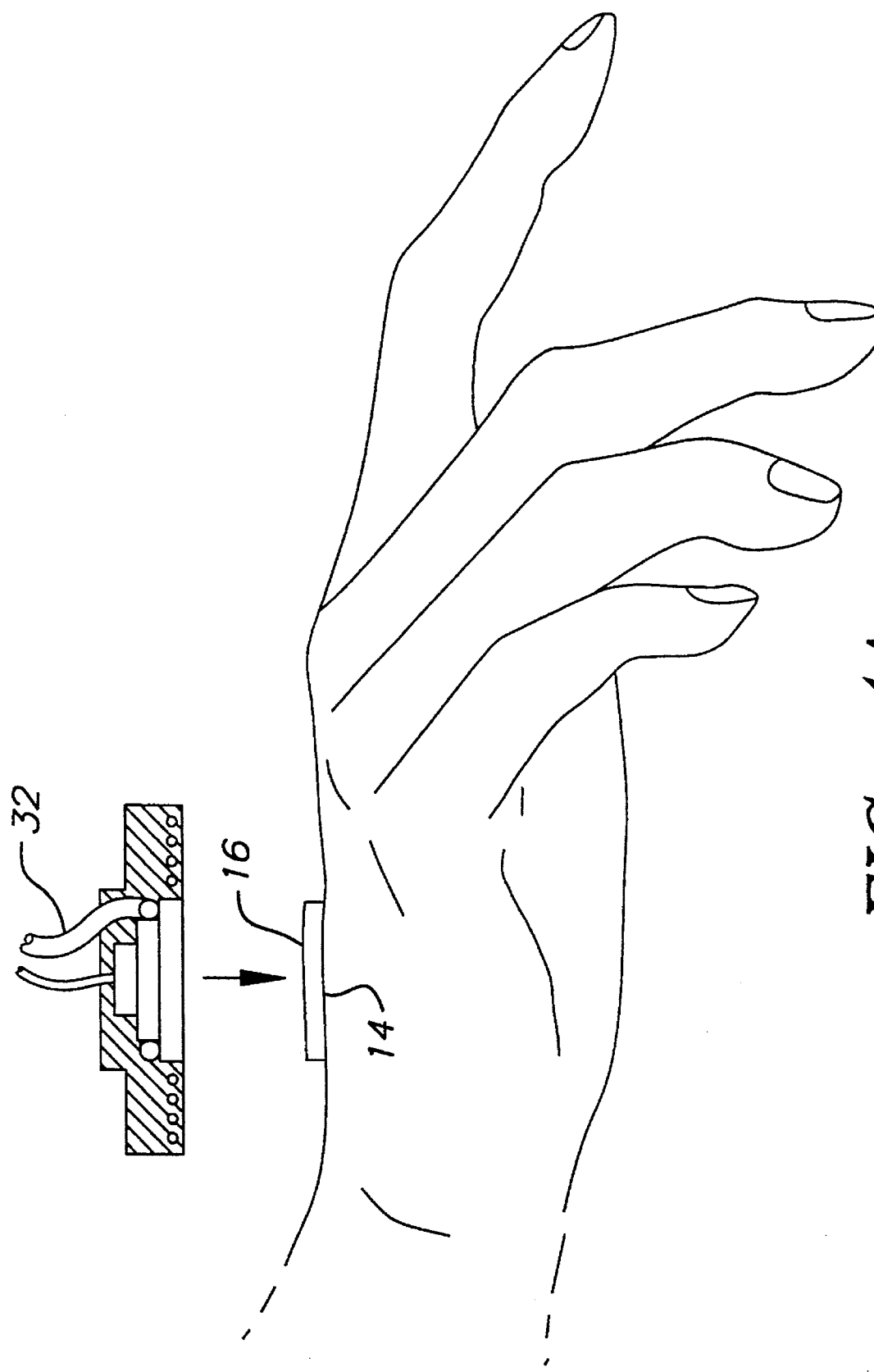
FIGS. 4B and 4A show the application of the device of the present invention to the hand of a patient.
Figure 4B:
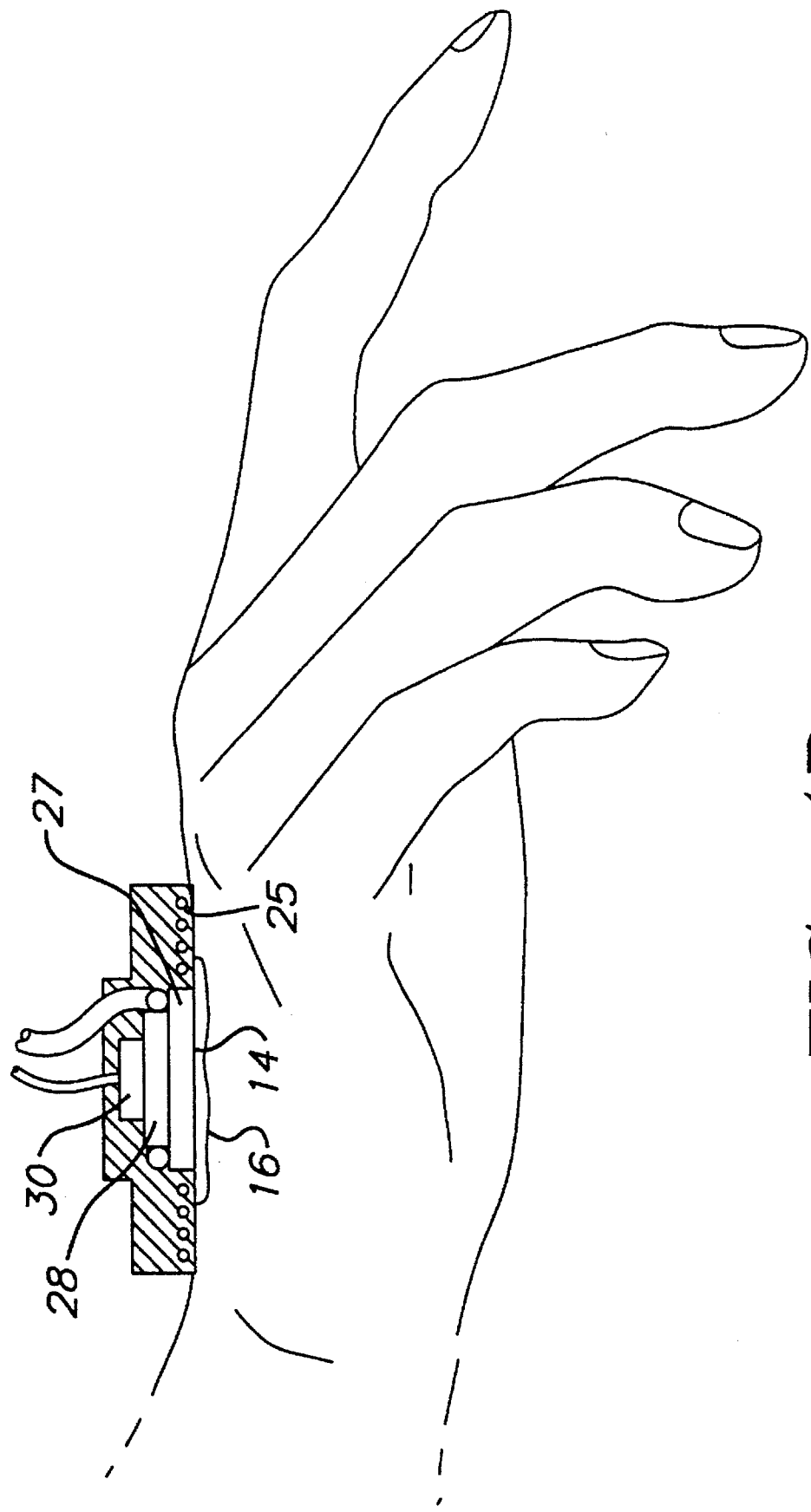

In yet a further embodiment shown in FIG. 3A, the device of the present invention could use a continuously modulated light source. In such an embodiment, a phase lock amplifier system 40 would be used to determine the decay (phase shift) between the excitation and fluorescence and thereby the phosphorescence decay constant (lifetime). The measurements could be repeated as rapidly (up to 40 to 100 times per second) or as slowly (once every few minutes) as needed. The present invention thus provides stable measurements of oxygen pressure over extended periods of time. The measured values of oxygen pressure can be presented in any form the user desires.

The temperature of the optical head in contact with the skin is regulated with a standard feedback control circuit. As shown in FIG. 1, thermistors 36 are mounted at the edge of the plastic cover and will measure the temperature and the signal compared to the desired signal. The differential heat signal is used to increase or decrease the heater current as needed to obtain or hold the set temperature by thermoregulation circuit 22.

The present invention thus-rapidly and accurately brings a part of the optical head which is in contact with the skin to a temperature between 39 and 42 degrees C and maintains it within plus or minus 0.1 degree C. The system can then measure oxygen pressure and tissue oxygenation. The invention requires no calibrations, adjustments or settings. Placement of the device is simple.

The operation of the present invention is now described. Initially, a site is selected for the placement of the device 10. A cream containing a phosphorescent probe 14 is applied to the skin of the patient. The oxygen impermeable film 16 is then placed over the cream. The apparatus of the present invention is then placed over the film 16. The heating element 25 heats the probe 14 and skin to a temperature between 39° and 42° C. The heating source 25 holds the device at a temperature slightly above normal body temperature in order to keep the vessels in the skin dilated. The excitation light 18 is flashed. The phosphorescent probe 14 is thereby excited and emits a phosphorescent light which is filtered by filter 28 and then detected by photodiode 30. The photodiode 30 then outputs a signal characteristic of the oxygen pressure of the patient which is processed by A/D converter 24 and analyzed by the microcomputer 26.

The present invention therefore measures the oxygen pressure at the surface of the skin. The measured oxygen pressures are closely correlated with the oxygen pressure in the capillary bed in the tissue and provide a measure of the integrated function of the performance of the cardio-pulmonary system. The measurements provided by the present invention are valuable assets in clinics, in intensive care units, in the care of soldiers in the field and in emergency care units.

The present invention has been described with reference to the enclosed preferred embodiment. It is to be appreciated that other embodiments fulfill the spirit and scope of the present invention and that the true nature and scope of the present invention is to be determined with reference to the claims appended hereto.

What is claimed is:

1. A system for measuring tissue oxygenation using oxygen dependent quenching phosphorescence comprising:

a phosphorescent probe applied to the surface of the skin of a patient;

an oxygen impermeable film placed over said probe and skin;

an optical head overlaying said oxygen impermeable film, said optical head comprising means for heating said impermeable film and said probe, means for providing an excitation light signal for exciting the probe such that said probe emits a phosphorescent light signal, and a photodiode circuit which detects the phosphorescent light emitted by the probe and which outputs a signal characteristic of the oxygen decay of said skin proximate to said reflected phosphorescent signal.

2. The system of claim 1 wherein said heating means comprises a heating coil.

3. The system of claim 2 wherein said heating means heats the device to a temperature of between 39 and 42 degrees centigrade.

4. The system of claim 1 further comprising a thermistor to control said heating element.

5. The system of claim 1 wherein said phosphorescent probe comprises phosphorescent molecules.

6. The system of claim 1 wherein said phosphorescent probe comprises a Pd-porphyrin.

7. Apparatus for measuring tissue oxygenation through the skin using oxygen dependent quenching of phosphorescence comprising:

a phosphorescent probe applied to the skin surface of a patient;

an oxygen impermeable film overlaying said probe and for isolating the area of skin with the phosphorescent probe from ambient oxygen;

an optical head overlaying said film, said optical head comprising a housing for covering said oxygen impermeable film and enclosing a light source for applying a single modulated excitation light for exciting said phosphorescent probe such that said probe emits an excitation light on the skin surface of said patient; a filter for filtering phosphorescent light from said skin; and a photodiode for receiving filtered phosphorescent light and for outputting an electrical signal characteristic of phosphorescent decay for the patient such that said decay is characteristic of the oxygen pressure of said patient.

8. The apparatus of claim 7 wherein said housing further encases means for heating the probe and skin.

9. Apparatus according to claim 6 wherein said outputted electrical signal is transmitted to an analog-to-digital converter.

10. Apparatus for measuring tissue oxygenation through the skin using oxygen dependent quenching of phosphorescence comprising:

a phosphorescent probe applied to the skin surface of a patient;

an oxygen impermeable polymeric film overlaying said probe for isolating the area of skin with the phosphorescent probe from ambient oxygen;

a housing enclosing an optical head, said housing comprising a plastic cover covering said oxygen impermeable film, a light source for applying a single modulated excitation light for exciting said phosphorescent probe such that said probe emits a light on the skin surface of said patient, a filter for filtering said emitted phosphorescent light, a photodiode for receiving filtered phosphorescent light and for outputting an electrical signal characteristic of phosphorescent light time and oxygen pressure for the patient and a heater for heating the probe and skin of the patient.

11. Apparatus according to claim 10 wherein said heating circuit heats said probe and skin to a temperature of between 39 and 42 degrees centigrade.

12. A method for measuring tissue oxygenation through the skin using oxygen dependent quenching of phosphorescence comprising:

applying a phosphorescent probe to the skin surface of a patient;

covering said probe with an oxygen impermeable film so as to isolate the area of skin with the phosphorescent probe from ambient oxygen;

applying a single modulated excitation light for exciting said phosphorescent probe such that said probe emits an excitation light on the skin surface of said patient caused by said excitation light;

filtering said emitted phosphorescent light; and outputting an electrical signal characteristic of phosphorescent decay time and the oxygen pressure for the patient.

* * * * *